United States Patent
Noor et al.

(10) Patent No.: US 11,877,959 B2
(45) Date of Patent: Jan. 23, 2024

(54) SLIDING JAW THRUST DEVICE

(71) Applicant: Rune Innovations Inc., Woodbridge, VA (US)

(72) Inventors: Abdul Noor, Woodbridge, VA (US); Ahmad Alach, Alexandria, VA (US); Fellipe Miqui, Sao Paulo (BR); Gautam Subramanian, Ashburn, VA (US); Louis Marmon, Washington, DC (US)

(73) Assignee: Rune Innovations Inc., Woodbridge, VA (US)

( * ) Notice: Subject to any disclaimer, the term of this patent is extended or adjusted under 35 U.S.C. 154(b) by 241 days.

(21) Appl. No.: 17/237,770

(22) Filed: Apr. 22, 2021

(65) Prior Publication Data
US 2021/0330538 A1 Oct. 28, 2021

Related U.S. Application Data

(60) Provisional application No. 63/014,171, filed on Apr. 23, 2020.

(51) Int. Cl.
*A61G 13/12* (2006.01)
*A61B 90/14* (2016.01)
(Continued)

(52) U.S. Cl.
CPC .......... *A61G 13/1215* (2013.01); *A61B 46/10* (2016.02); *A61B 90/14* (2016.02);
(Continued)

(58) Field of Classification Search
CPC .......... A61G 13/1215; A61G 2200/327; A61G 2210/00; A61B 46/10; A61B 90/14; A61B 2090/502
(Continued)

(56) References Cited

U.S. PATENT DOCUMENTS 3,461,858 A * 8/1969 Irving .................. A61H 31/008
206/572
3,737,660 A * 6/1973 Ando .................... A61B 90/14
378/39

(Continued)

FOREIGN PATENT DOCUMENTS

| CN | 1631328 A | * | 6/2005 | |
| CN | 208426388 U | * | 1/2019 | .......... A61H 31/008 |
| DE | 102017120245 A | * | 3/2019 | ............. A61B 90/50 |

OTHER PUBLICATIONS

Mechanisms X (Double-rack Gear-Lever Mechanism 2, Nov. 12, 2016, https://www.youtube.com/watch?v=0TDOnohgCzo) (Year: 2016).*

(Continued)

*Primary Examiner* — Ophelia A Hawthorne
*Assistant Examiner* — Michael Milo
(74) *Attorney, Agent, or Firm* — DLA PIPER LLP (US)

(57) ABSTRACT

A device and method that facilitates performance of a jaw thrust maneuver. A base connected to a rack and pinion mechanism including at least one pinion rotatably attached to the base and at least two racks slidably attached to the base and engaged with the pinion to move in opposite directions upon rotation of at least one pinion. A pair of arms, each pivotably coupled to one of the racks to allow rotational freedom of motion. A patient's head is placed in supine position and a pair of arms slides towards the patient's head in synchrony to position the arms to clear the patient's airways.

20 Claims, 10 Drawing Sheets (51) Int. Cl.
  *A61B 46/10* (2016.01)
  *A61B 90/50* (2016.01)
(52) U.S. Cl.
  CPC .. *A61B 2090/502* (2016.02); *A61G 2200/327* (2013.01); *A61G 2210/00* (2013.01)
(58) Field of Classification Search
  USPC .......................................................... 128/869
  See application file for complete search history.

(56) References Cited

U.S. PATENT DOCUMENTS

| | | | |
|---|---|---|---|
| 5,524,639 A * | 6/1996 | Lanier | A61G 13/12 |
| | | | 128/870 |
| 7,004,528 B2 | 2/2006 | Nye | |
| 7,290,369 B2 | 11/2007 | Tarrega Lloret | |
| 8,191,553 B2 | 6/2012 | Haworth | |
| 9,072,612 B2 | 7/2015 | Sethi | |
| 9,125,745 B2 | 9/2015 | Deshpande | |
| 9,173,765 B2 | 11/2015 | Haworth | |
| 2003/0216230 A1 | 11/2003 | Wang | |
| 2008/0006278 A1 * | 1/2008 | Henke-Sarmento | A61B 46/10 |
| | | | 128/849 |
| 2008/0153056 A1 | 6/2008 | Baldwin | |
| 2010/0307509 A1 * | 12/2010 | King | A61G 13/1215 |
| | | | 128/845 |
| 2013/0092177 A1 * | 4/2013 | Chua | A61B 46/10 |
| | | | 53/429 |
| 2013/0190604 A1 * | 7/2013 | Moffatt | A61B 6/4441 |
| | | | 600/411 |
| 2015/0053212 A1 | 2/2015 | Guerra | |
| 2015/0164726 A1 | 6/2015 | Ward | |
| 2016/0101008 A1 | 4/2016 | Haworth | |
| 2016/0361220 A1 * | 12/2016 | Sexton | A61G 13/126 |

OTHER PUBLICATIONS

Jaw Elevation Device, Sharn Anesthesia Inc, Apr. 27, 2021, 2 pgs. https://www.sharn.com/foam-patient-positions/p/JawElevationDevice/.

* cited by examiner

SLIDING JAW THRUST DEVICE

CROSS REFERENCE TO RELATED APPLICATION

This application claims priority to U.S. Provisional Application No. 63/014,171 filed Apr. 23, 2020, the entire disclosure of which is incorporated by reference herein.

BACKGROUND

In the postoperative period, airway management may be considered. General anesthesia may relax the tongue and jaw muscles, making airway management more difficult for the medical care team due to obstruction of the airway. This may necessitate a procedure called the jaw thrust maneuver, which may be conducted for 10-15 minutes as the patient awakens. When the jaw thrust maneuver is performed successfully, the jaw of the patient is pushed forward opening the mouth. By pushing the jaw forward the tongue may also be pushed forward preventing blockage of a patient's airway.

DETAILED DESCRIPTION

Briefly described, and according to one embodiment, aspects of the present disclosure generally relate to devices, systems, apparatuses, and methods for surgical and postoperative airway management. In various embodiments, the disclosed device (also referred to herein as the "Sliding Jaw Thrust Device" or "SJTD") may provide a mechanism that allows for implementation of the jaw thrust maneuver for keeping a patient's airway clear.

Figure 1:
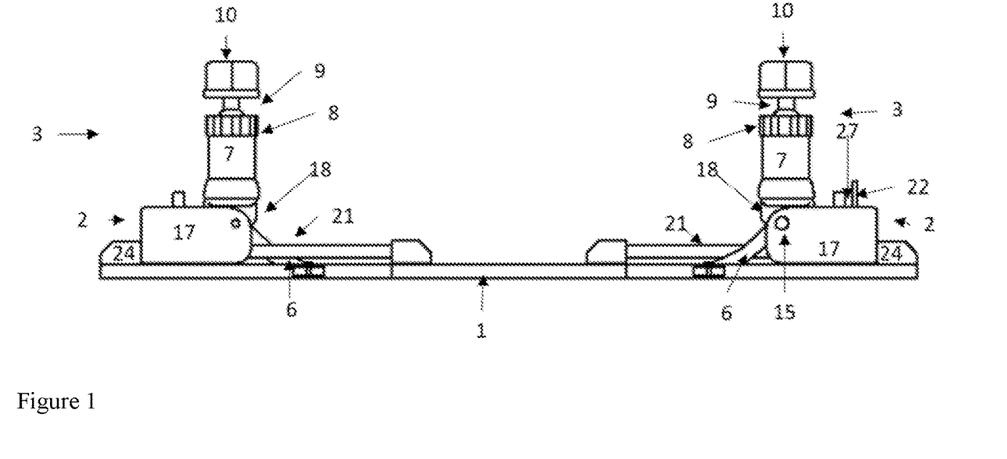
FIG. 1 shows a side elevation view of an embodiment of the invention.

The embodiment shown in FIG. 1 may be operated by a medical professional or any lay person to perform the jaw thrust maneuver. By operating the device, this method of performing the jaw thrust maneuver may standardize the process, minimizing risks of errors and increasing the standard of care for the maneuver. Additionally, the SJTD may return critically valuable time for medical professionals by the streamlined method.

Figure 2:
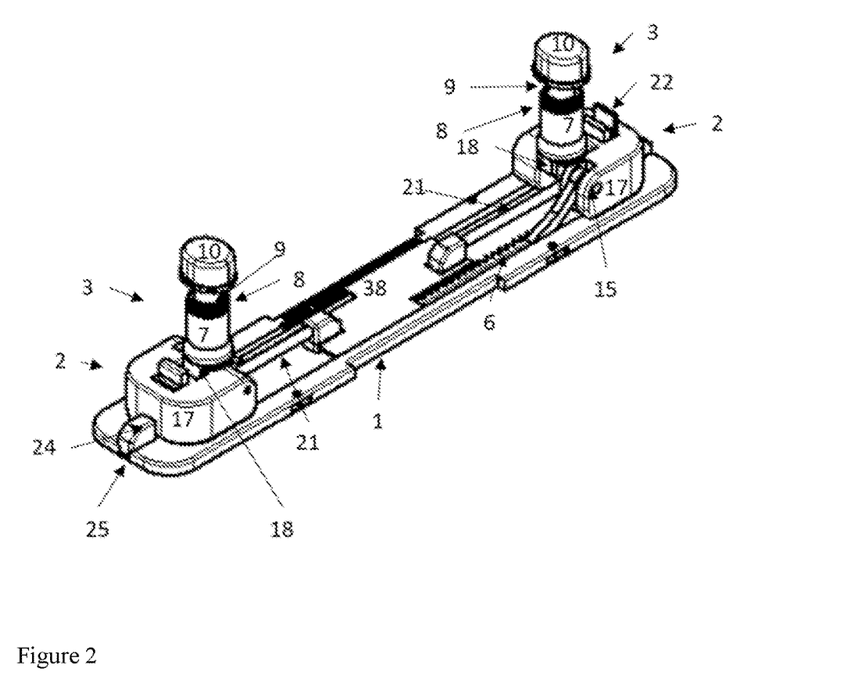
FIG. 2 shows a perspective view of the embodiment of FIG. 1.
Figure 3:
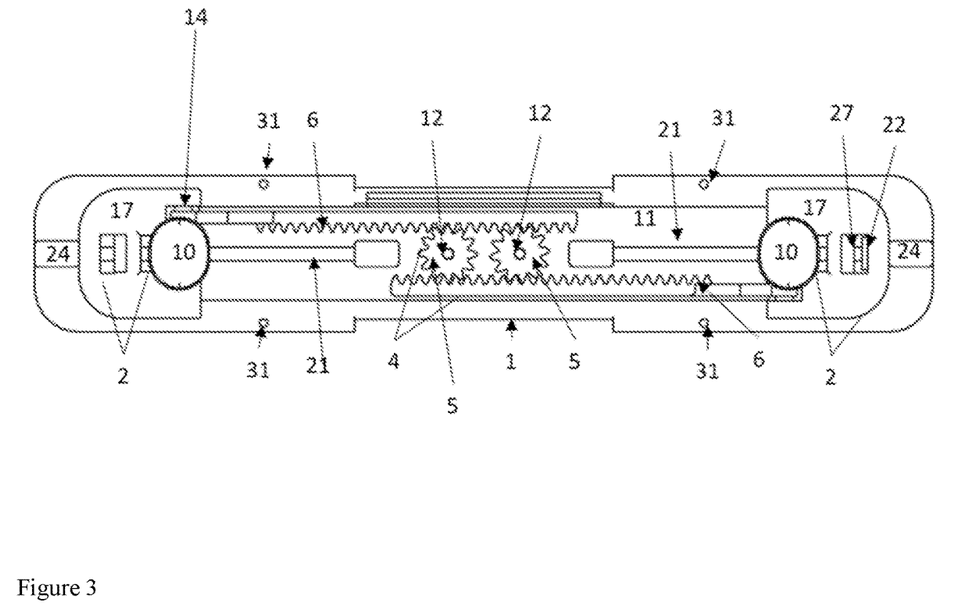
FIG. 3 shows a top-down view of the embodiment of FIG. 1.
Figure 5:
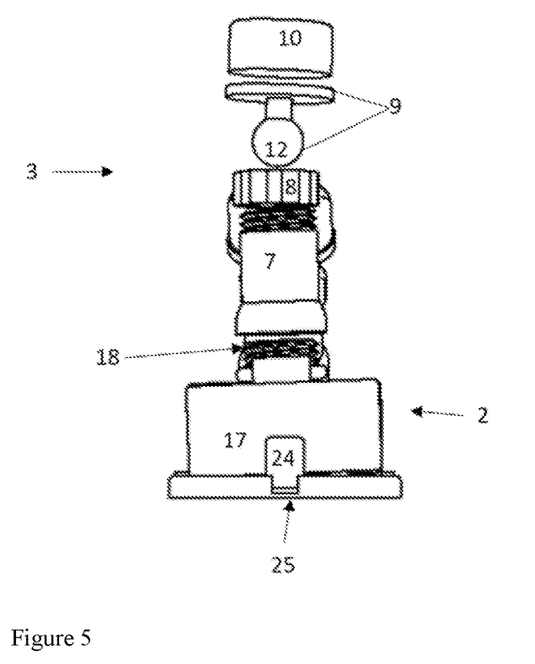
FIG. 5 shows a side elevation view of an arm suitable for teenager and adult patients for an embodiment.
Figure 9:
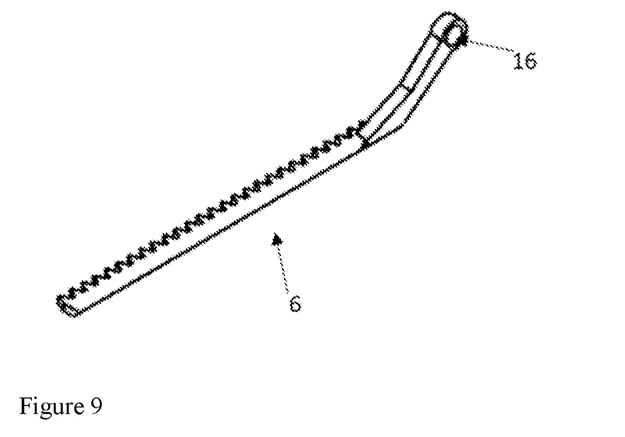
FIG. 9 shows a perspective view of a rack for a rack and pinion system of the embodiment of FIG. 1.
Figure 10:
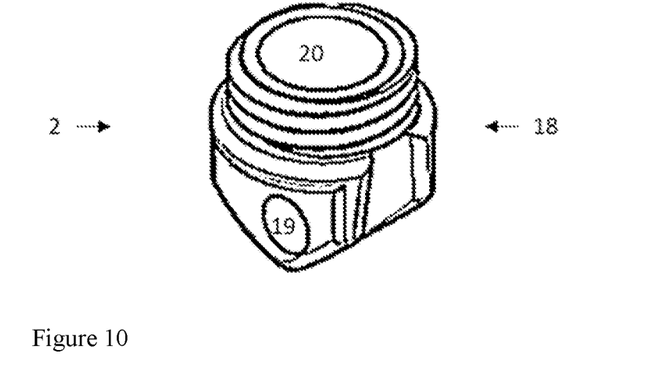
FIG. 10 shows a perspective view of an arm connector mechanism for connecting the side arm holder to the arm of the embodiment of FIG. 1.
Figure 14:
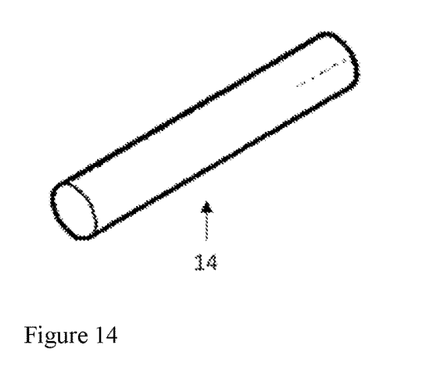
FIG. 14 shows a perspective view of a holding rod to attach the side arm holder to the rack of the embodiment of FIG. 1.
Figure 18:
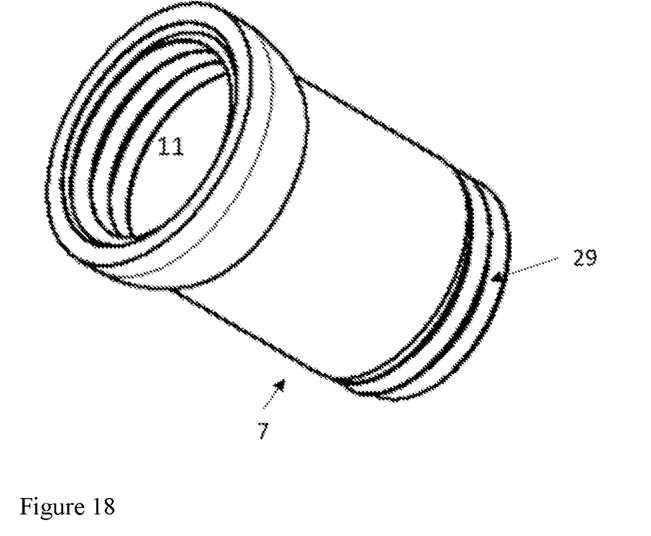
FIG. 18 shows a perspective view of a connecting body for the arm of the embodiment of FIG. 1.

With reference to an embodiment of the disclosure in FIG. 1 base 1 serves to hold other components. Base 1 may house a rack and pinion mechanism 4 in a trench 11 on base 1 top side as shown in FIG. 3. As shown in FIG. 3, two pinions 5 are rotatably coupled to shafts 12 in base 1. As shown in FIG. 3, two racks 6 are placed at opposite ends of base 1 and operatively coupled with pinions 5. A pair of arm holders 2 are positioned at opposite ends of base 1 and attached to one of racks 6, respectively. Each arm holder 2 includes two components: arm holder base 17 (see FIG. 7) and arm connector 18 (see FIG. 10). In the embodiment of FIG. 1, arm holders 2 are connected to racks 6 by holding rods 14. FIG. 14 shows an embodiment of holding rod 14. Holding rod 14 (see FIG. 14) attaches through holes 15 (see FIGS. 1, 2 and 7) in arm holders 2 and holes 16 in rack 6 (see FIG. 9). A pair of arms 3 are attached to arm holders 2. FIG. 5 shows arm 3 attached to arm holder 2 of the embodiment in FIG. 1. Arm holder 2 and arms 3 have threaded ends to be screwed onto each other (see. FIGS. 10 and 18). Other embodiments may use different connection techniques such as a snap on mechanism or use of magnets.

Base 1 of the disclosure may be any of multiple embodiments. Base 1 may be made of a variety of materials including wood, plastic, and metals. For use in specific medical situations involving a Magnetic Resonance Imaging (MRI) Device, Base 1 may be made of MRI safe material such as plastic, titanium, nonmagnetic, or paramagnetic materials. A base cover (plastic snap on cover image not included) 38 may be attached to base 1 as shown in FIG. 2. A variety of base covers can be used. Base cover 38 in FIG. 2 snaps onto base 1 to cover up rack and pinion mechanism 4. Alternative embodiments of base 1 may include additional customizable holes or attachment features.

Figure 8:
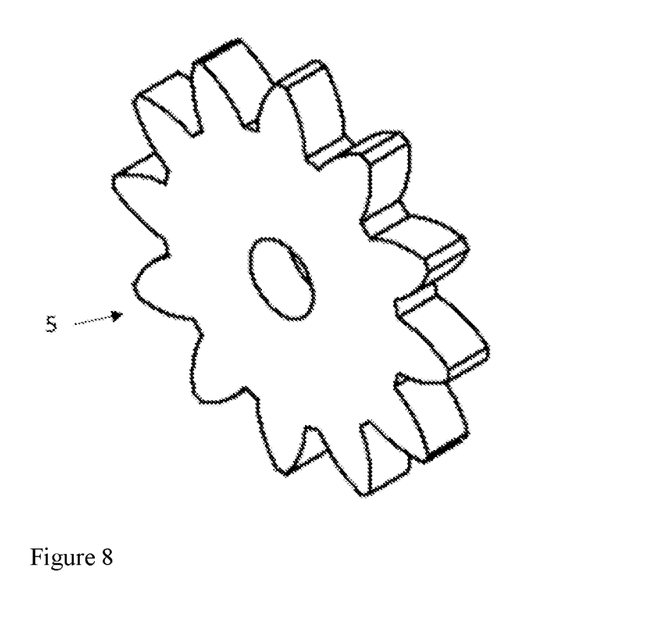
FIG. 8 shows a perspective view of a pinion gear for a rack and pinion system of the embodiment of FIG. 1.

Rack and pinion mechanism 4 provides the ability for arms 3 to slide in the SJTD. FIG. 8 shows a pinion gear 5. One or more pinion gears 5 can be used in different embodiments of the SJTD. FIG. 3 shows an embodiment utilizing two pinion gears 5. Each pinion gear 5 in the embodiment of FIG. 3 connects to a shaft 12 of base 1 in trench 11 and can rotate in either direction. FIG. 9 shows an embodiment of rack 6 that operatively couples with at least one pinion gear 5. The rack and pinion mechanism 4 may be made of a variety of materials including plastics and metals. For use in specific medical situations involving a Magnetic Resonance Imaging (MRI) Device, rack and pinion mechanism 4 may be made of MRI safe material such as plastic, titanium, nonmagnetic, or paramagnetic materials.

Rack and pinion mechanism 4 allows for synchronous movement of arms 3. Racks 6 are coupled to arms 3. In the embodiment shown in FIG. 5, a pair of arms 3 are attached to a pair of arm holders 2 through a screw on mechanism (see FIGS. 10 and 18). Arm holders 2 are attached to racks 6 using a holding rod 14 (see FIG. 14). Alternate embodiments of arms 3 may be directly attached to the racks 6 themselves using a holding rod 14 (see FIG. 14) or other types of attachment mechanisms such as screws. As one of arms 3 slides with rack 6 the other arm 3 will slide in the opposite direction with the other rack 6. This function allows a single hand to operate the embodiment. When arm 3 moves with rack 6, at least one pinion gear 5 rotates causing the opposite arm holder 2 to move in the opposite direction. Alternate embodiments may include the use of more than two pinions 5 or the use of more than two racks 6.

Figure 4:
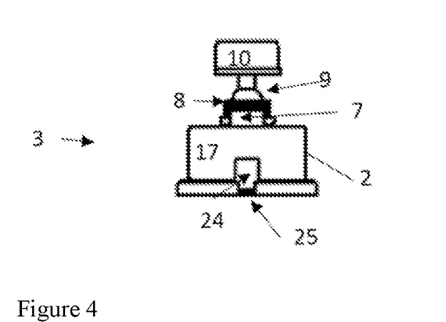
FIG. 4 shows a side elevation view of an arm suitable for adolescent patients for an embodiment.
Figure 6:
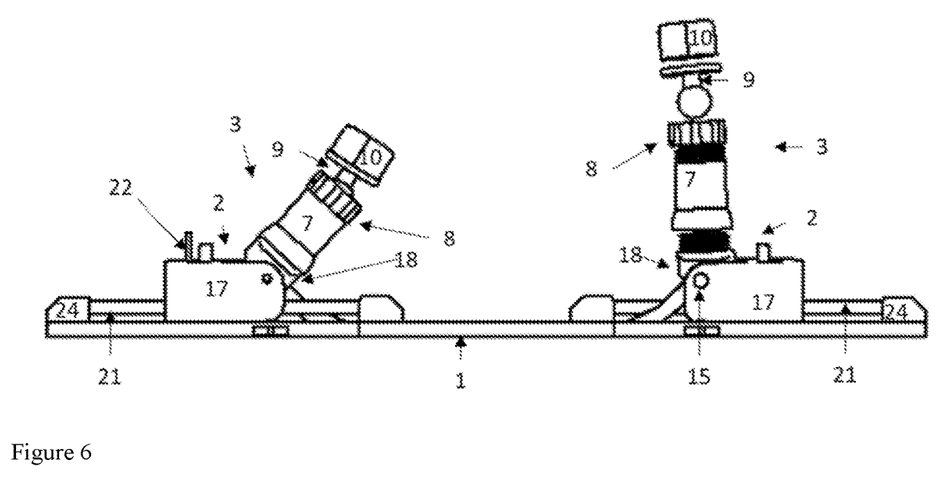
FIG. 6 shows a side elevation view of an embodiment with arms at different angles of FIG. 1.
Figure 17:
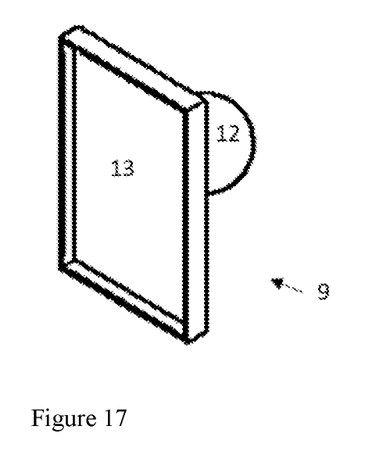
FIG. 17 shows a perspective view of an arm ball joint mechanism for the arm of the embodiment of FIG. 1.

Arms 3 of the SJTD allow for a range of pivoting movement to position arms 3 into the correct position to perform the jaw thrust maneuver. Arms 3, as shown in FIG. 6, allow for movement towards a 90° from a longitudinal axis of base 1. In some embodiments arms 3 are prevented from moving past a 90° angle by arm holder 2. Arm 3, shown in FIG. 5, contains four components: a connecting body 7, a locking cap 8, an arm ball joint mechanism 9, and an arm padding 10. FIG. 17 shows an embodiment of an arm ball joint mechanism 9 and FIG. 18 shows an embodiment of a connecting body 7. A connecting body 7 has one threaded end 11 to screw onto arm holders 2 (see FIG. 10) and another threaded end 29 to attach a locking cap 8. A locking cap 8 screws onto connecting body 7. Ball portion 12 of ball joint mechanism 9 is captured behind locking cap 8. An arm padding 10 is adhered to the top 13 of ball joint mechanism 9. Arm padding 10 may be attached to the top 13 of ball joint mechanism 9 using adhesive or other type of connective mechanism. As the embodiment in FIG. 6 shows, ball joint mechanism 9 may pivot relative to connecting body 7. Arm padding 10 provides a comfortable contact point when arms 3 make contact with the patient. Arm paddings 10 may be made of a variety of materials, but compressible materials would be preferred for the patient's comfort. The embodiment shown in FIG. 6 utilizes a gel material for an arm padding 10. Arms 3 may be made of a variety of materials including wood, plastic, and metals. For use in specific medical situations involving a Magnetic Resonance Imaging (MRI) Device, arms 3 may be made of MRI safe material such as plastic, titanium, nonmagnetic, or paramagnetic materials. Arms 3 shown FIG. 6 represent one embodiment of an arm to create the pivoting motion, alternate embodiments could forgo any of the components shown in FIG. 6. Alternate embodiments of arms 3, as shown in FIG. 4 and FIG. 5, comes in different sizes to accommodate the specific patient's needs based on age or other specifications. FIG. 4 shows a smaller arm for adolescent patients compared to the arm shown in FIG. 5 for teenager and adult patients.

Figure 7:
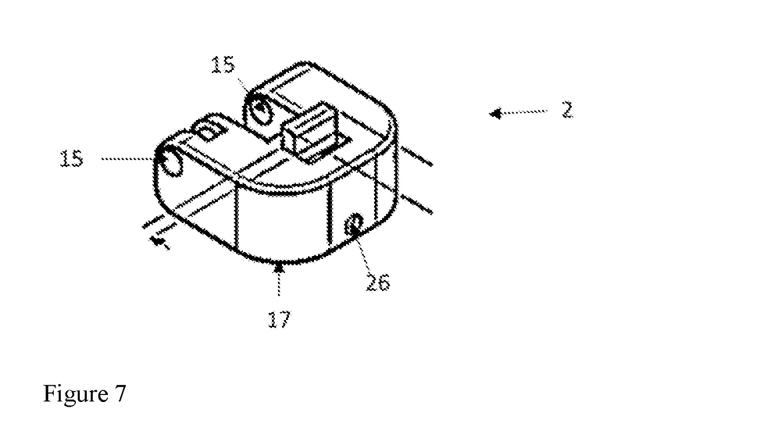
FIG. 7 shows a perspective view of an arm holder base of the embodiment of FIG. 1.

Some embodiments of the disclosure may use arm holders 2 to couple arms 3 to rack and pinion mechanism 4. FIG. 1 shows an embodiment of arm holders 2 containing two components: an arm holder base 17 and an arm connector 18. FIG. 7 shows an embodiment of arm holder base 17 and FIG. 10 shows an embodiment of arm connector 18. Holes 15 in the arm holder base are aligned with holes 16 in rack 6 and holes 19 in arm connector 18. A holding rod 14 (see FIG. 14) goes through holes 15 in arm holder base 17 (see FIG. 7), hole 16 in rack 6 (see FIG. 9) and holes 19 in an arm connector 18 (see FIG. 10) to link all the components together. Arm connector 18 contains a threaded end 20 that screws together with connecting body 7 to connect arm 3 with arm holder 2 as shown in FIG. 5. Alternate embodiments may be used to connect arm holders 2 to arms 3 such as a pin or holding rod mechanism. Threaded end 20 of arm connector 18 allows for a variety of arms 3 to be attached to arm bases 2. For example, FIG. 3 and FIG. 4 represent different embodiments of arm 3 that may alternately be attached to the same arm holders 2. Arms holders 2 may be made of a variety of materials including wood, plastic, and metals. For use in specific medical situations involving a Magnetic Resonance Imaging (MRI) Device, a pair of arms holders 2 may be made of MRI safe material such as plastic, titanium, nonmagnetic, or paramagnetic materials.

Figure 13:
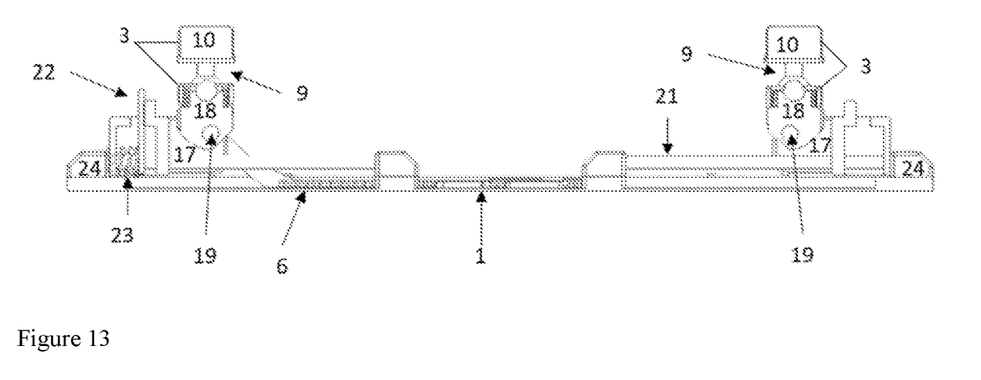
FIG. 13 shows a half-section side view of an embodiment utilizing a rail catch mechanism.
Figure 15:
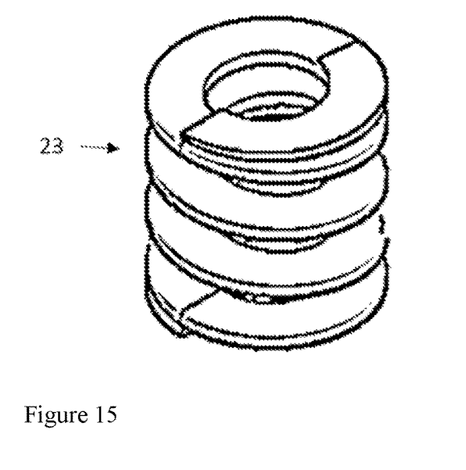
FIG. 15 shows a perspective view of a compression spring of the embodiment of FIG. 1 and FIG. 13.
Figure 16:
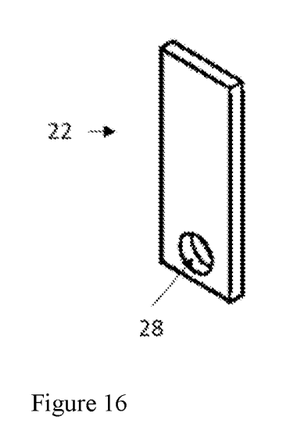
FIG. 16 shows a perspective view of a rail catch of the embodiment of FIG. 1 and FIG. 13.

FIG. 13 shows on embodiment of a lock mechanism used to lock the positions of arm holders 2. Alternate embodiments of lock mechanisms may be used, and some embodiments may not be a part of arm holders 2. The lock mechanism in FIG. 13 utilizes a rail 21, a rail catch 22, and a compression spring 23. FIG. 16 shows rail catch 22 and FIG. 15 shows compression spring 23. The compression spring 23 is within arm holder base 17 and aligns with hole 26 (see FIG. 7) in arm holder base 17. As shown in FIG. 7, rail catch 22 is inserted into an opening 27 in arm holder base 17 so that compression spring 23 is between the side of arm holder base 17 and rail catch 22. FIG. 1 shows a rail holder 24 containing rail 21 connected to base 1 by sliding and locking into a slot 25 (see FIG. 2) of base 1. Rail 21 is inserted through hole 26 of arm holder base 17, hole 28 of rail catch 22 and compression spring 23. Rail catch 22 is biased by compression spring 23 against rail 21, locking arms 3 and preventing additional movement along a longitudinal axis. A user may push rail catch 22 against compression spring 23 to release the lock, allowing arms 3 to move. Alternative embodiment may utilize a switch or other mechanisms to release the lock. In FIG. 13, one rail catch 22 and compression spring 23 is utilized, but alternative embodiment may have a rail catch 22 and compression spring 23 in both arm holders 2. Alternate embodiments may be used to lock arms 3 in place such as inserting groves into base 1 to lock arms 3 at predefined positions. A locking mechanism may be made of a variety of materials including wood, plastic, and metals. For use in specific medical situations involving a Magnetic Resonance Imaging (MRI) Device, a lock mechanism may be made of MRI safe material such as plastic, titanium, nonmagnetic, or paramagnetic materials.

Figure 11:
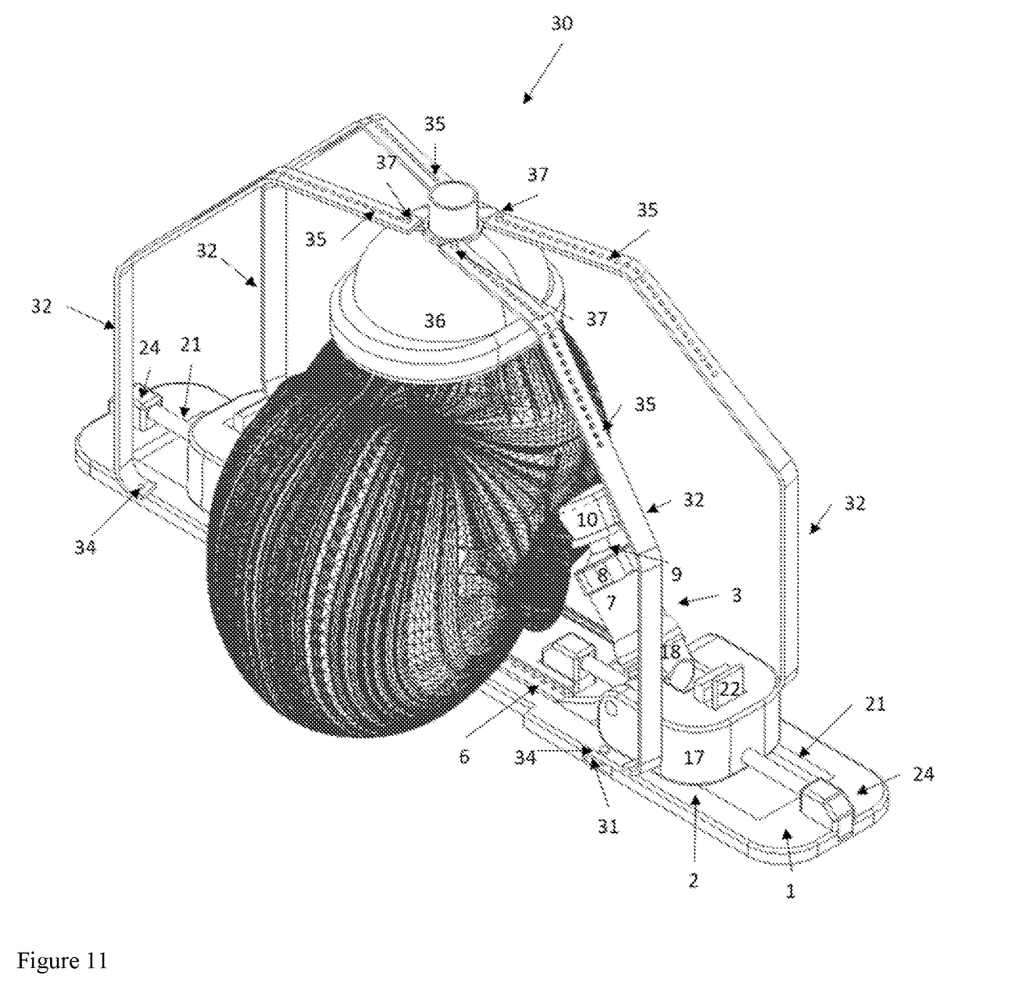
FIG. 11 shows a perspective view of an embodiment with a mask attachment.
Figure 12:
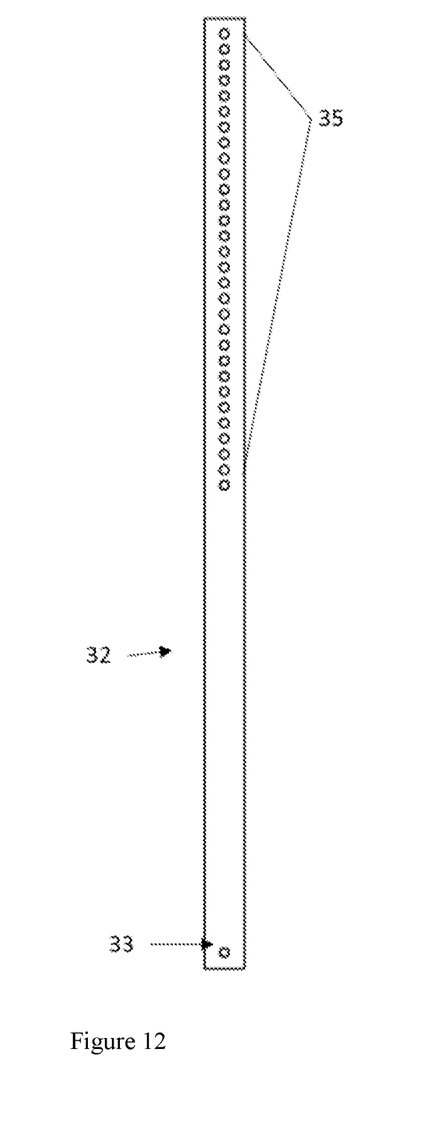
FIG. 12 shows a side elevation view of a mask strap of the embodiment of FIG. 11

In some embodiments as shown in FIG. 11, base 1 may accommodate a mask attachment mechanism 30. FIG. 3 shows four holes 31 to connect mask straps 32. The embodiment shown in FIG. 11 utilizes pins 34 to attach a hole 33 (see FIG. 12). in a mask strap to hole 31 in base 1. In alternative embodiments, a mask attachment mechanism 30 may be attached to base 1 in different ways such as a screw on mechanism. Base 1 may accommodate a variety of different type of mask straps in different embodiments. FIG. 12 shows a mask strap 32 use in the embodiment of FIG. 11. Mask strap 32 in FIG. 12 contains equally spaced-out holes 35 to customize the position of a mask. FIG. 11 shows the use of an anesthetic mask 36 using pins 37 to attach to the spaced-out holes 35 for a mask attachment device, but any type of mask with varying attachment mechanisms may work in different embodiments.

Figure 19:
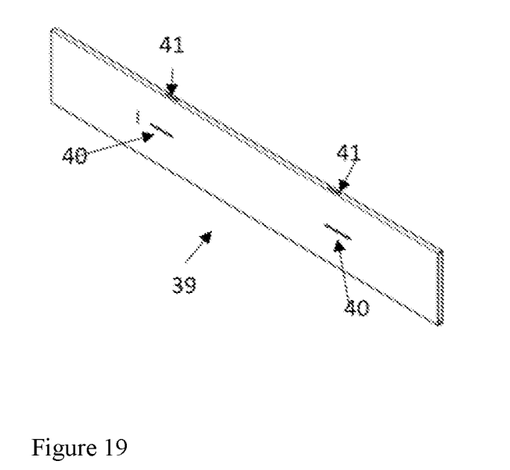
FIG. 19 shows a perspective view of a device cloth cover of the embodiment of FIG. 1 and FIG. 11.

In a hospital setting there exists a risk of environment or bodily contaminants coming into contact with the SJTD. In certain embodiments of the SJTD, as shown in FIG. 19, a device cover 39 may be added to reduce the contaminant problem. An elastic fabric material may be used for the cover to fit the form of the SJTD properly. FIG. 19 shows two holes 40 for arms 3 to fit through, thereby eliminating interference with arm operations. Holes 41 may be added to device cover 39 for mask straps 32 to fit through accommodating mask attachment mechanism 30. The material used could be water and moisture resistant to prevent contamination. After utilizing the SJTD, the device cover can be taken off and washed if needed to clean off the contaminant and be reusable again. A device cover material may be made with material for MRI environments including plastics, nonmagnetic or paramagnetic materials.

In operation an individual may place a patient's head in a supine position. The patient's head may be placed on any surface including a pillow for comfort or elevated slightly. Arms 3 used for the patient are appropriately sized for the patient's head depending on age and other specifications. Arms 3 may be pushed and slid towards the patient's head and may be pivoted towards a 90° angle relative to the longitudinal axis of base 1 against the bend of the jaw of the patient to free up the patient's airways as shown in FIG. 11. Rack and pinion mechanism 4 provides the force to move arms 3 in unison along base 1 toward the patient's head. When arms 3 are in the correct position, arms 3 are locked against movement along the longitudinal axis of base 1, so the patient's mouth is opened, and the airways cleared without the need for a medical professional to hold the jaw's positioning. FIG. 13 shows an embodiment utilizing rail 21 and rail catch 22 to lock arms 3. In certain embodiments, the SJTD has a mask strap 32 shown in FIG. 11. A mask may be attached to the mask strap 32 as shown in FIG. 11 and then positioned on the patient's face depending on the medical circumstances such as a need for anesthesia. When the patient no longer requires the jaw thrust maneuver, arms 3 are unlocked and return to their original positions.

What is claimed is:

1. A device comprising:
    a base;
    a rack and pinion mechanism including at least one pinion rotatably attached to the base and at least two racks slidably coupled to the base and engaged with the at least one pinion to move equidistantly in opposite directions upon rotation of the at least one pinion;
    a pair of arms, each pivotably coupled to one of the racks, respectively;
    a pair of arm holders, each pivotably coupled to one of the racks, respective ones of the arms being detachably coupled to respective ones of the arm holders; and
    at least one lock detachably coupled to at least one of the arm holders, the at least one lock comprising:
        at least one rail holder coupled to the base adjacent to at least one outer edge of the base;
        at least one rail attached to the base by the at least one rail holder and coupled to at least one of the arm holders,
        at least one rail catch coupled to the at least one rail, and
        at least one compression spring between the at least one rail catch and the at least one arm holder and configured to be releasably biased against the at least one rail and thereby lock the at least one arm holder from movement while biased.

2. The device of claim 1, further comprising arm paddings attached to a top of the arms.

3. The device of claim 2, wherein the arm padding is comprised of compressible material.

4. The device of claim 3, wherein the compressible material includes gel material.

5. The device of claim 1, further comprising a device cover configured to cover the base wherein the device cover contains holes for the arms.

6. The device of claim 5, wherein the device cover is made of elastic, water and moisture resistance material, and is machine washable.

7. The device of claim 5, wherein the device cover contains holes for mask straps.

8. The device of claim 5, wherein the device cover is comprised of Magnetic Resonance Imaging safe material.

9. The device of claim 1, further comprising a mask attachment mechanism including at least one strap coupled to the base and configured to retain a mask in a sealed position on a user's face.

10. The device of claim 9, wherein the at least one mask strap contains spaced out holes configured for mask attachment.

11. The device of claim 1, wherein the device is comprised of Magnetic Resonance Imaging safe material.

12. The device of claim 11, wherein the Magnetic Resonance Imaging safe material includes at least one of plastic, titanium, or another nonmagnetic or para-magnetic material.

13. The device of claim 1, wherein:
    the at least one pinion comprises at least two pinions; and
    the at least two racks slidably are configured to move equidistantly in opposite directions upon rotation of the at least two pinions, such that a manipulation to move a first one of the at least two racks results in an equidistant and opposite movement of a second one of the at least two racks.

14. The device of claim 13, wherein the at least two pinions are aligned along an axis parallel to the opposite directions of movement of the at least two racks.

15. The device of claim 1, wherein different sizes of the arms can be attached to the pair of arm holders.

16. The device of claim 1, wherein the lock further comprises a switch configured to release the rail catch.

17. A method comprising:
    positioning a patient's head in supine position;
    coupling an appropriately sized arm for the patient's head to each of at least two racks slidably coupled to a base, the racks being coupled to at least one pinion configured to enable movement of the racks equidistantly in opposite directions;
    sliding the arms along the base towards the patient's head;
    pivoting the arms in a direction toward a 90° position from a longitudinal axis of the base to push the patient's jaw upwards; and
    locking the arms longitudinally in place by biasing at least one compression spring of a lock mechanism comprising:
        at least one rail holder coupled to the base adjacent to at least one outer edge of the base;
        at least one rail attached to the base by the at least one rail holder and coupled to an arm holder of at least one of the arms,
        at least one rail catch coupled to the at least one rail, and
        the at least one compression spring between the at least one rail catch and the arm holder.

18. The method of claim 17, further comprising:
    attaching a mask to at least one mask strap coupled to the base; and
    attaching the mask to the patient's face.

19. The method of claim 17, further comprising:
    removing the arms from arm holders slidably attached to the base and each coupled to one of the racks, respectively; and
    attaching different arms of a different size to the arm holders.

20. The method of claim 17, further comprising releasing the compression spring to unlock the arms.

\* \* \* \* \*